United States Patent [19]

Mälson

[11] Patent Number: 4,764,360

[45] Date of Patent: Aug. 16, 1988

[54] COMPOSITION FOR OPHTHALMOLOGICAL USE

[75] Inventor: Tomas Mälson, Uppsala, Sweden

[73] Assignee: Pharmacia AB, Uppsala, Sweden

[21] Appl. No.: 878,832

[22] PCT Filed: Oct. 23, 1985

[86] PCT No.: PCT/SE85/00410

§ 371 Date: Apr. 30, 1986

§ 102(e) Date: Apr. 30, 1986

[87] PCT Pub. No.: WO86/02548

PCT Pub. Date: May 9, 1986

[30] Foreign Application Priority Data

Nov. 1, 1984 [SE] Sweden ............................. 8405464

[51] Int. Cl.$^4$ ...................... A61K 9/08; A61K 47/00; A61K 49/00
[52] U.S. Cl. ............................................. 424/2; 424/2
[58] Field of Search ............................................ 424/2

[56] References Cited

FOREIGN PATENT DOCUMENTS 1091056 5/1984 U.S.S.R. .

*Primary Examiner*—Nancy A. B. Swisher
*Attorney, Agent, or Firm*—Fred Philpitt

[57] ABSTRACT

A composition to be used in ophthalmology and containing an aqueous solution of a high molecular polymer to which has been added a polymeric dye having a molecular weight higher than 10,000.

4 Claims, No Drawings

COMPOSITION FOR OPHTHALMOLOGICAL USE

This invention is concerned with a colored composition to be used in ophthalmology and consisting of an aqueous solution of a high molecular polymer to which a polymeric dyestuff has been added.

Viscoelastic solutions of highly purified hyaluronic acid (Healon ®, Pharmacia AB, Uppsala, Sweden) are nowadays commonly employed in eye surgery practice. Examples of such surgical operations are corneal transplantations, cataract surgery and glaucoma surgery, the Healon ® being injected into the anterior eye chamber in order to maintain that chamber in its correct shape during the operation. For vitrectomy and in cases of retinal detachment the substance is similarly injected into the vitreous chamber (i.e. the space normally occupied by the vitreous humor) so that then the injected substance, in cooperation with residual vitreous humor, will retain the retina in a properly fixed position.

Healon ® is a solution that is entirely clear and colorless. These properties while being excellent-in themselves nevertheless do have the drawback that the substance is not readily observable during the operation and cannot be clearly distinguished from e.g. natural vitreous humor and aqueous humor inasmuch as both of these have approximately the same optical properties as Healon ®. Therefore, in order to facilitate inspection during the operation, Zirm (Klin. Mbl. Augenheilk. 181 (1982), 426–428) has reported a series of tests employing fluorescein additions to Healon ®.

Furthermore also methyl cellulose has been tested in eye surgery despite the fact that it has different properties in some respects. Methyl cellulose, too, is a colorless substance, and for this reason Fechner et al. have carried out experiments (British Journal Ophthalmology 67 (1983) 259-263) in which solutions of the polymeric substance are stained with patent blue (patent blue V; Martindale: The Extra Pharmacopoeia 27th ed. London, Pharmaceutical Press, 1977:475) when employed in eye lens implantation surgery.

However, the eye surgeon's work has not really been facilitated to any major extent by the aforesaid attempts at improving the discernibility of the solution of polymeric substance in the eye, where in addition to said polymeric substance—that is, hyaluronic acid or methyl cellulose—there are other components present which have similar optical properties. The reason for the substantial failure of such attempts is that dyes of the aforesaid type are capable of diffusing out of the polymer rather quickly, thereby bestowing their color on surrounding tissue. This in turn means that it will be very difficult to discern details during the course of an operation where such a prior art product has been applied. Moreover in case fluorescein is used this involves the necessity of irradiating the area with a UV lamp in order to render the dye and thus the polymer solution visible to inspection. This irradiation however is a somewhat undesirable expedient since it may have a negative effect on sensitive tissue in the patient's eye.

Thus there is a true need for staining methods by which solutions of polymeric substances of the hyaluronic acid or methyl cellulose type can be stained in a manner such that (i) the dye is maintained clear in the solution and (ii) if by any chance some of the dye leaks out it will not stain the surrounding tissue.

We have now found that a composition having the desired properties is obtained if the added dye is a sufficiently high molecular weight polymeric substance which is soluble in the composition. Consequently this invention relates to a colored composition consisting of a solution of a high molecular polymer to which has been added a dye having a molecular weight of at least 10,000.

Examples of the high molecular polymer are given in prior art literature, with Healon ® being the foremost representative; but methyl cellulose, too, is an example of a useful polymer.

The polymeric dye should be hydrophilic and have a molecular weight exceeding 10,000, preferably exceeding 30,000. Advantageously the molecular weight will be very high, but it is limited by the solubility prerequisite; a practical upper limit is about $10 \times 10^6$. The polymeric dye may be chosen from among a plurality of hydrophilic non-toxic dyes. Examples of conceivably useful substances and processes for their production have been described by e.g. Dawson, D. J., in Aldrichimia Acta 14 (1981), 23–29. Of particular interest here is the method involving reaction between a polymeric carrier molecule and a dye, inasmuch as this provides the possibility of manufacturing polymeric dyes of widely different properties depending on inter alia the carrier molecule chosen.

A very important point is that the polymeric dye must not exhibit any toxic, inflammatory or other undesirable reactions in the eye. Furthermore it is important that phase separations or other complications are avoided when the dye is admixed with the polymeric substance. The types of dyes and reactions which are useful for the substitution of the polymeric carrier molecules are well known to the artisan. Dyestuffs especially simple in use are those containing reactive groups, for example chlorotriazine groups. Among these dyestuffs, called "reactive dyes", may be mentioned products having the commercial names of Procion ®, Cibacron ®, Reacton ® and Remazol ®, these being just a few examples of available products.

The carrier molecule may be chosen from among a great number of compounds as will be readily apparent to a person skilled in the art when acquainted with the general concept of the present invention. The molecular weight should exceed about 10,000. Examples of such suitable compounds are water-soluble polysaccharides such as e.g. dextran or derivatives thereof, for example carboxy, hydroxy, propyl or hydroxyethyl dextran, cellulose derivatives, for example carboxymethyl or methyl cellulose, starch or starch derivatives and pullulan; furthermore proteins such as e.g. human serum albumin or gelatin, and synthetic polymers such as for example polyvinyl pyrrolidone, polyvinyl alcohol, polyethylene glycol, polypropylene glycol and polyvinyl amine.

Compositions according to the present invention are suitably prepared in that a polymeric dye, preferably dissolved in water, is added to an aqueous solution of a high polymer substance of a known per se kind—e.g. consisting of an aqueous solution containing hyaluronic acid or methyl cellulose—whereupon the components are mixed so as to form a homogeneous solution. The polymeric dye employed has a molecular weight of at least 10,000, and according to a preferred embodiment this dye has been prepared by reacting a polymeric carrier molecule with a dyestuff belonging to the group of reactive dyes. In carrying out this reaction it is possible in a manner known per se to vary the degree of substitution ad libitum, i.e. too freely choose the desired number of dyestuff molecules per molecule of polymeric carrier.

As regards the amount of polymeric dye to be present in the composition, this is chosen so that the composition as such will be visually readily distinguishable from the eye tissue but will not have an absorbance which is so high as to conceal the tissue lying underneath. Preferred concentration ranges are entirely dependent on the particular dyestuff chosen and on the degree to which the polymeric substance is substituted therewith; this range can readily be determined by means of some simple tests.

When a colored composition of the present novel type is employed this will make it much easier to monitor an injection of e.g. Healon ® with respect to the exact location of the injection and the spreading pattern, as compared to the cases where colorless prior art products are employed. Moreover it is easier, whenever Healon ® is to be removed, to evaluate the amount of Healon ® retained in the eye (if any) and its location. Similarly, a progressive elimination of Healon ® may be effectively monitored postoperatively.

The invention also relates to a method of facilitating observation of an aqueous solution which has been administered in the eye and contains a polymeric substance, in that an improved observability is obtained due to the fact that said solution additionally contains a polymeric dye of the above-described kind.

The invention will be further illustrated by the below examples which however are entirely non-limitative.

EXAMPLE 1

Preparation of Cibacron ® Blue F3GA - dextran ("blue dextran")

40 g of dextran (MW about 70,000) was dissolved in 200 ml of water. Then 18 g of Cibacron ® Blue F3GA and 1.2 g of sodium hydroxide were added. The solution was stirred at 45° C. overnight, whereupon it was neutralized with acetic acid. For purifying the colored polymer from unreacted dye the polymer was precipitated repeatedly in ethanol. After four reprecipitations, gel filtration on Sephadex ® G 25 showed that the product then consisted entirely of a high molecular fraction, without any traces of non-bound dye. The product was dried at 70° C. in vacuo. The degree of substitution of the blue dextran was ascertained spectrophotometrically and was found at 620 nm to amount to 0.044 dyestuff molecules per repeating glucose unit.

EXAMPLE 2

Preparation of colored hyaluronic acid solutions

Blue dextran from Example 1 was dissolved in physiological saline (0.276 g $Na_2HPO_4 \cdot 2H_2O$, 0,0395 g $NaH_2PO_4 \cdot H_2O$ and 8.476 g NaCl dissolved in water to give 100 ml of solution; pH 7.3). To the solution thus obtained was then added sodium hyaluronate of MW about $3 \times 10^6$, to a concentration of 10 mg/ml. The blue dextran concentration was 1 mg/ml.

The sodium hyaluronate was dissolved by slow rotation end over end for two days. The composition was a clear viscous blue solution.

EXAMPLE 3

Applying a composition of this invention to eyes of rabbits

Rabbits used in this test were pigmented specimens for the most part, Sandy Lop ♀, plus a few albinos. The rabbits were anesthetized, and a local anesthetic was applied to the cornea. A colored hyaluronic acid composition prepared in accordance with Example 2 or in an analogous manner was implanted in the rabbit eye by injection of the solution into the anterior chamber, with simultaneous withdrawal of aqueous humor therefrom (about 300 µl). It was found that when blue dextran was employed having an 0.044 degree of substitution (Example 1) the concentration must be higher than about 0.04%, whereas concentrations exceeding 0.2% will give a product that is too dark. A preferred content therefore is within the range of about 0.07–0.12%. A preparation containing a green dextran obtained by staining dextran with equal amounts of Cibacron ® Blue and Cibacron ® Yellow was found to have good optical properties at a concentration of about 0.4%. The degree of substitution in this case was estimated to be 0.03. The same value was obtained with fluorescein isothiocyanate-dextran (FITC-dextran from Pharmacia, Uppsala, Sweden) having a degree of substitution of about 0.009.

EXAMPLE 4

Comparison with prior art method employing low molecular dyestuffs

A hyaluronic acid composition containing patent blue (CI 42051) was prepared in that a solution of the dye was mixed with sodium hyaluronate to give a patent blue concentration of 0.1 mg/ml and a sodium hyaluronate concentration of 10 mg/ml. The resultant product was a clear, viscous, blue solution.

In a similar manner a hyaluronic acid composition was prepared containing methylene blue (CI 52105), the concentration of this dye in the product being 0.05 mg/ml. In this case the product was a mixture containing some small undissolved fragments.

When the hyaluronic acid compositions each containing one of said low molecular dyes were implanted in rabbit eye anterior chambers, in a manner analogous to Example 3, this resulted in staining of the vicinal tissue, especially the cornea, during the 2 to 3 hours that the solution was present in the chamber.

Diffusion test

The equipment employed was a modified diffusion cell of the type described by Sundelöof, L.O. Analytical Biochemistry 127 (1982), 282. The hyaluronic acid compositions were prepared in a manner analogous to Examples 2 and 4 respectively, but with a 10 times higher concentration of the dye. A 1 % solution of blue dextran in 1 % sodium hyaluronate was introduced into the lower half of one cell; an 0.1 % solution of patent blue in 1 % hyaluronic acid was introduced into the lower half of the other cell. The overlayer solution employed in both cells was phosphate-buffered physiological saline. After 60 minutes the degree of blue coloring of the overlayer solution was measured spectrophotometrically, and the diffusion constant D was calculated according to the method described by Sundelöf. Results:

D of blue dextran is $15 \times 10^{-12}$ m²/s

D of patent blue is $367 \times 10^{-12}$ m²/s

The polymeric dye thus has a much lower diffusion rate in the polymer solution.

I claim:

1. A composition to be used in ophthalmology and containing an aqueous solution of a high molecular polymer, said composition containing additionally at least one dissolved polymeric dye which has a molecular weight exceeding 10,000 and is present in an amount such that the composition when applied in the eye is visually observable while at the same time still permitting visual observation of tissue lying underneath.

2. A composition according to claim 1 in which said polymer is hyaluronic acid.

3. A composition according to claim 1 in which said polymer is a cellulose derivative, for example methyl cellulose.

4. A composition according to claim 1 in which said polymer dye is dextran having a dye coupled to it.

* * * * *